US010214980B2

(12) United States Patent
Orban et al.

(10) Patent No.: US 10,214,980 B2
(45) Date of Patent: Feb. 26, 2019

(54) MEASURING FLUID PROPERTIES IN A DOWNHOLE TOOL

(71) Applicant: Schlumberger Technology Corporation, Sugar Land, TX (US)

(72) Inventors: Jacques Orban, Katy, TX (US); R. Craig Boswell, Draper, UT (US); Scott Richard Woolston, Spanish Fork, UT (US); Jordan Dane Englund, Provo, UT (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 501 days.

(21) Appl. No.: 14/741,584

(22) Filed: Jun. 17, 2015

(65) Prior Publication Data
US 2015/0376963 A1    Dec. 31, 2015

Related U.S. Application Data

(60) Provisional application No. 62/018,743, filed on Jun. 30, 2014.

(51) Int. Cl.
*E21B 21/08* (2006.01)
*E21B 47/10* (2012.01)
(Continued)

(52) U.S. Cl.
CPC ............. *E21B 21/08* (2013.01); *E21B 7/28* (2013.01); *E21B 10/32* (2013.01); *E21B 47/10* (2013.01);
(Continued)

(58) Field of Classification Search
CPC .... E21B 21/08; E21B 49/08; E21B 2049/085; E21B 47/10; G01N 11/00; G01N 11/14;
(Continued)

(56) References Cited

U.S. PATENT DOCUMENTS 2,894,590 A    7/1959  Johnson et al.
3,053,087 A *  9/1962  Waugh .................... G01F 1/115
                                              73/861.78
(Continued)

FOREIGN PATENT DOCUMENTS

GB    2102129 A  *  1/1983  ............. G01F 1/075
GB    2460096 A     11/2009
(Continued)

OTHER PUBLICATIONS

Notification of Transmittal of the International Search Report and the Written Opinion of the International Searching Authority in International Patent Application No. PCT/US2014/027527, dated Jul. 3, 2014, 10 pages, Korean Intellectual Property Office, Republic of Korea.
(Continued)

*Primary Examiner* — Jennifer H Gay

(57) ABSTRACT

A sensor assembly may include a housing made of a non-magnetic material. The housing may define an interior chamber. A shaft may extend from the housing. A bearing may be positioned around the shaft. An impeller may be positioned around the shaft and the bearing, and the impeller may include a magnetized portion. A sensor may be positioned within the interior chamber and/or proximate the magnetized portion. The sensor may detect the magnetized portion of the impeller to sense a rate of rotation of the impeller. The rate of rotation of the impeller may correspond to changes in flow rate of the fluid. As the flow rate of the fluid, and the rate of rotation of the impeller change in predetermined manners, control signals may be conveyed to activate a tool.

10 Claims, 8 Drawing Sheets

(51) Int. Cl.
  *E21B 7/28* (2006.01)
  *E21B 10/32* (2006.01)
  *G01N 11/00* (2006.01)
  *G01F 1/115* (2006.01)

(52) U.S. Cl.
  CPC .............. *G01N 11/00* (2013.01); *G01F 1/115* (2013.01); *G01N 2011/0053* (2013.01)

(58) Field of Classification Search
  CPC ...... G01N 2011/0046; G01N 2011/147; G01F 1/115; G01F 1/075; G01F 1/3236; G01F 1/32
  See application file for complete search history.

(56) References Cited

U.S. PATENT DOCUMENTS

| | | | | |
|---|---|---|---|---|
| 3,162,042 | A * | 12/1964 | Hart | G01F 1/115 73/152.35 |
| 3,163,038 | A * | 12/1964 | Bryant | G01F 1/10 166/330 |
| 3,238,776 | A * | 3/1966 | Potter | G01F 1/10 384/397 |
| 3,542,441 | A * | 11/1970 | Nixon | F16C 17/02 384/312 |
| 3,894,590 | A | 7/1975 | Takano et al. | |
| 4,358,253 | A * | 11/1982 | Okano | F01D 25/166 384/368 |
| 4,560,014 | A | 12/1985 | Geeczy | |
| 4,566,317 | A * | 1/1986 | Shakra | E21B 47/10 73/152.35 |
| 4,825,421 | A | 4/1989 | Jeter | |
| 4,871,301 | A * | 10/1989 | Buse | F04D 29/0413 415/175 |
| 4,880,320 | A * | 11/1989 | Haines | F01D 25/164 384/119 |
| 4,902,144 | A * | 2/1990 | Thoren | F01D 25/166 384/287 |
| 4,903,533 | A * | 2/1990 | Kato | G01F 1/115 384/370 |
| 4,918,996 | A * | 4/1990 | Kato | G01F 1/115 384/402 |
| 5,109,705 | A * | 5/1992 | Masyagutov | G01F 1/10 73/861.83 |
| 5,228,786 | A * | 7/1993 | Tanimoto | F16C 19/163 384/492 |
| 5,450,760 | A * | 9/1995 | Lew | G01F 1/106 73/861.02 |
| 5,533,811 | A * | 7/1996 | Polch | F16C 33/1085 384/107 |
| 5,683,185 | A * | 11/1997 | Buse | F16C 33/08 384/255 |
| 5,685,797 | A * | 11/1997 | Barnsby | F16C 33/12 384/625 |
| 6,002,643 | A | 12/1999 | Tchakarov et al. | |
| 6,109,372 | A | 8/2000 | Dorel et al. | |
| 6,732,617 | B2 | 5/2004 | Steinweg et al. | |
| 6,732,817 | B2 | 5/2004 | Dewey et al. | |
| 7,351,034 | B2 * | 4/2008 | Cens | G01F 1/115 416/205 |
| 7,401,572 | B2 * | 7/2008 | Donehue | G01F 1/115 116/264 |
| 7,573,397 | B2 | 8/2009 | Petrovic et al. | |
| 7,793,499 | B2 * | 9/2010 | Gutknecht | F01D 25/166 184/6.11 |
| 8,205,509 | B2 * | 6/2012 | Oddie | E21B 47/10 73/152.18 |
| 8,365,821 | B2 | 2/2013 | Hall et al. | |
| 8,511,404 | B2 | 8/2013 | Rasheed | |
| 9,447,676 | B2 * | 9/2016 | Rasheed | E21B 10/32 |
| 9,528,324 | B2 | 12/2016 | Fuller et al. | |
| 9,556,682 | B2 | 1/2017 | Fuller et al. | |
| 9,726,589 | B2 * | 8/2017 | Zamora | G01N 11/14 |
| 2003/0079913 | A1 | 5/2003 | Eppink et al. | |
| 2004/0134687 | A1 | 7/2004 | Radford et al. | |
| 2004/0222022 | A1 | 11/2004 | Nevlud et al. | |
| 2005/0229718 | A1 * | 10/2005 | Cens | G01F 1/115 73/861.79 |
| 2006/0120859 | A1 * | 6/2006 | Cens | G01F 1/115 415/170.1 |
| 2007/0134106 | A1 * | 6/2007 | McKeirnan, Jr. | F01D 25/16 417/407 |
| 2007/0204787 | A1 * | 9/2007 | Donehue | G01F 1/115 116/273 |
| 2008/0128169 | A1 | 6/2008 | Radford et al. | |
| 2008/0134774 | A1 * | 6/2008 | Oddie | G01V 11/005 73/152.01 |
| 2008/0253888 | A1 * | 10/2008 | Hsiao | H02K 1/185 415/229 |
| 2009/0114448 | A1 | 5/2009 | Laird et al. | |
| 2010/0089583 | A1 | 4/2010 | Xu et al. | |
| 2010/0116034 | A1 * | 5/2010 | Abbott | G01N 11/14 73/54.35 |
| 2010/0154530 | A1 * | 6/2010 | Oddie | E21B 47/10 73/152.35 |
| 2010/0309746 | A1 * | 12/2010 | Andersson | B01F 7/003 366/165.3 |
| 2011/0127044 | A1 | 6/2011 | Radford et al. | |
| 2011/0226531 | A1 * | 9/2011 | Jones | E21B 47/082 175/50 |
| 2012/0011928 | A1 * | 1/2012 | Wootten | E21B 47/10 73/152.29 |
| 2012/0080231 | A1 | 4/2012 | Radford et al. | |
| 2012/0273187 | A1 | 11/2012 | Hall et al. | |
| 2012/0308174 | A1 * | 12/2012 | Head | E21B 17/023 385/13 |
| 2012/0308365 | A1 * | 12/2012 | Woollenweber | F01D 25/16 415/170.1 |
| 2013/0020092 | A1 * | 1/2013 | Ramon | E21B 23/01 166/381 |
| 2013/0084035 | A1 * | 4/2013 | Williams | F16C 33/6659 384/472 |
| 2013/0127273 | A1 * | 5/2013 | Lee | G11B 19/2036 310/90 |
| 2013/0206401 | A1 | 8/2013 | Bhoite et al. | |
| 2013/0306373 | A1 * | 11/2013 | Rasheed | E21B 10/32 175/24 |
| 2014/0260560 | A1 * | 9/2014 | Zamora | G01N 11/14 73/54.28 |
| 2014/0262508 | A1 | 9/2014 | Fuller et al. | |
| 2014/0262525 | A1 | 9/2014 | Fuller et al. | |
| 2014/0332270 | A1 * | 11/2014 | Odell, II | E21B 10/322 175/40 |
| 2015/0233299 | A1 * | 8/2015 | Chekansky | F02C 7/28 60/605.1 |
| 2015/0376963 | A1 * | 12/2015 | Orban | G01N 11/00 175/48 |
| 2016/0084301 | A1 * | 3/2016 | Baldassarre | F16C 25/02 384/103 |
| 2017/0051606 | A1 * | 2/2017 | Fanini | E21B 47/10 |
| 2017/0101824 | A1 | 4/2017 | Fuller et al. | |
| 2017/0227388 | A1 * | 8/2017 | Vigneaux | E21B 49/08 |

FOREIGN PATENT DOCUMENTS

WO    WO-9505581 A1 *    2/1995    ............ G01F 1/10
WO    WO2008150290 A1    12/2008

OTHER PUBLICATIONS

Notification of Transmittal of the International Search Report and the Written Opinion of the International Searching Authority in International Patent Application No. PCT/US2014/027634, dated Aug. 14, 2014, 17 pages, Korean Intellectual Property Office, Republic of Korea.

International Search Report issued in internationsi patent application PCT/US2015/037320 dated Sep. 25, 2015, 3 pages.

(56) References Cited

OTHER PUBLICATIONS

International Preliminary Report on Patentability issued in International Patent Application No. PCT/US2014/027634 dated Sep. 15, 2015.
European Search Report issued in European Patent Application No. 14768506.9 dated Mar. 22, 2016, 4 pages.
Communication Pursuant to Article 94(3) issued in European Patent Application No. 14768506.9 dated Apr. 13, 2016, 5 pages.
Office Action issued in U.S. Appl. No. 14/208,639 dated Jun. 8, 2016, 12 pages.
Office Action issued in U.S. Appl. No. 15/379,690 dated Mar. 28, 2018, 13 pages.
Office Action issued in U.S. Appl. No. 15/379,690 dated Nov. 13, 2017, 10 pages.
Office Action issued in U.S. Appl. No. 14/208,512 dated Feb. 5, 2016, 12 pages.
International Preliminary Report on Patentability issued in International Patent Application No. PCT/US2014/027527 dated Sep. 15, 2015.
European Search and Examination Report issued in European Patent Application No. 14768849.3 dated Mar. 9, 2016, 6 pages.
European Search Report issued in European Patent Application No. 14768849.3 dated Feb. 12, 2016, 4 pages.
International Preliminary Report on Patentability issued in International Patent Application No. PCT/US2015/037320 dated Jan. 3, 2017, 13 pages.

\* cited by examiner

MEASURING FLUID PROPERTIES IN A DOWNHOLE TOOL

CROSS-REFERENCE TO RELATED APPLICATIONS

This application claims the benefit of, and priority to, U.S. Patent Application Ser. No. 62/018,743, filed Jun. 30, 2014, which application is expressly incorporated herein by this reference in its entirety.

BACKGROUND

During downhole operations, such as drilling and reaming, drilling fluid is pumped through a drill string to a downhole tool. The fluid flows into the annulus of the wellbore through one or more ports or nozzles in a drill bit or other downhole component. The fluid then flows back up to the surface through the annulus, which is located between the downhole tool and the wellbore wall. In a drilling, milling, underreaming, or other similar operation, the fluid may carry cuttings or swarf back to the surface.

In some downhole operations, the fluid may flow into the wellbore annulus through ports or nozzles installed in reamers or flow splitter tools. The properties of the fluid (e.g., flow rate, viscosity, density) may affect the performance of the downhole tool. For example, the properties of the fluid may affect the drag on the downhole tool, the attenuation of mud pulse telemetry signals transmitted from or received by the downhole tool, the output of turbines and/or motors in the downhole tool, and the like. Flow meters, viscometers, densitometers, and other downhole fluid sensors may be used to measure the properties of the fluid (e.g., flow rate, viscosity, and density, respectively).

SUMMARY

In accordance with some embodiments of the present disclosure, a sensor assembly is disclosed. The sensor assembly may include a housing and a shaft extending from the housing. Bearings may be positioned around the shaft, while an impeller may be positioned around the shaft and the bearings. The impeller may include a marker, and sensor of the sensor assembly may be proximate the marker and used to detect the marker to sense a rotational velocity of the impeller.

In a further embodiment, a downhole tool may include a body having a bore passing axially through a full or partial length of the body. A sensor assembly may be positioned in the bore, and may include a housing, a shaft coupled to the housing, a bearing around the shaft, an impeller around the shaft and the bearing, and a sensor. The housing may be made of a non-magnetic material and the impeller may include a magnetized portion. The sensor may be proximate the magnetized portion or within the interior chamber, and may detect the magnetized portion of the impeller. An electronics assembly may be positioned in the bore and may receive and decode a signal from the sensor assembly indicative of a rate of rotation of the impeller, an axial distance between the impeller and the sensor, or both. An actuation assembly may be positioned in the bore and actuate a mechanical device between at least two states in response to the signal.

In accordance with another embodiment of the present disclosure, a method for measuring a property of a fluid in a wellbore may include running a downhole tool into a wellbore. The downhole tool may include a sensor assembly and an electronics assembly. The sensor assembly may include a housing made of a non-magnetic material and may have an interior chamber. A shaft may extend from the housing, and a bearing may be positioned around the shaft. An impeller may be positioned around the shaft and the bearing, and may include a magnetized portion. A spring may be positioned axially between the bearing and the housing, and the spring may compress when an axial force is applied to the impeller. A sensor of the sensor assembly may sense a rate of rotation of the impeller, measure the axial force on the impeller, or both. As fluid is pumped into the wellbore, the fluid may cause the impeller to rotate. A property of the fluid may then be determined with the electronics assembly by using data related to the rotation of the impeller.

According to yet another embodiment of the present disclosure, a method for measuring a property of a fluid may include running a downhole tool into a wellbore. The downhole tool may have a sensor assembly and an electronics assembly. The sensor assembly may include a housing with an interior chamber. The housing may also be made of a non-magnetic material. A shaft may extend from the housing and a bearing may be positioned around the shaft. An impeller may be positioned around the shaft and the bearing. The impeller may include a marker to allow a position of the impeller to be detected. A hydraulic brake may be coupled to the first impeller, and may include a fin that is about parallel to a central longitudinal axis extending through the impeller. The fin may slow a rate of rotation of the impeller when the hydraulic brake is coupled to the impeller. A sensor may sense the rate at which the impeller rotates in response to the flow of fluid pumped into the wellbore. A flow rate and a density of the fluid may be determined with the electronics assembly using data related to the rotation of the impeller.

In still another embodiment, a method for activating a downhole tool may include running a downhole tool into a wellbore. The downhole tool may include a housing, a shaft extending from the housing, and an impeller around the shaft. A sensor may also be included and may sense a rotational speed of the impeller. To activate the downhole tool, fluid may be pumped into the wellbore, which may cause the impeller to rotate. A flow rate of the fluid may be determined by sensing the rotational speed of the impeller. The flow rate may also be varied, and the changes can be detected using the impeller and sensor. The flow rate as it changes may be compared to a predetermined flow rate, and a mechanical device can be activated when the flow rate satisfies a predetermined condition.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

So that the recited features may be understood in detail, a more particular description may be had by reference to one or more embodiments, some of which are illustrated in the appended drawings. It is to be noted, however, that the appended drawings are illustrative embodiments, and are, therefore, not to be considered limiting of the scope of the present disclosure or the claims.

FIGS. 5-1 and 5-2 are illustrative calibration charts for determining an average velocity and an apparent viscosity of a fluid, respectively, according to one or more embodiments disclosed herein.

FIG. 6-1 is a cross-sectional view of the sensor assembly shown in FIGS. 2 and 3 with a brake, according to one or more embodiments disclosed herein.

FIG. 6-2 is a front end view of the brake of FIG. 6-1, according to one or more embodiments disclosed herein.

FIG. 6-3 is a cross-sectional view of a downhole tool including two sensor assemblies that are axially offset from one another in a wellbore, with one of the sensor assemblies including an impeller with a brake coupled thereto, and another one of the sensor assemblies including an impeller not having a brake coupled thereto, according to one or more embodiments disclosed herein.

FIG. 7-1 is an illustrative graph showing an estimated density of a fluid based on a difference between a rotation rate of an impeller with and without a brake, according to one or more embodiments disclosed herein.

FIG. 7-2 is an illustrative graph showing an estimated density of a fluid based on a difference between an axial drag force on an impeller with and without a brake, according to one or more embodiments disclosed herein.

DETAILED DESCRIPTION

Some embodiments described herein generally relate to downhole tools. More particularly, some embodiments disclosed relate to systems and methods for measuring the properties of fluid flowing through a downhole tool. Further still, some embodiments of the present disclosure relate to actuating a downhole tool in response to measuring property of fluid flowing through a downhole tool.

Figure 1:
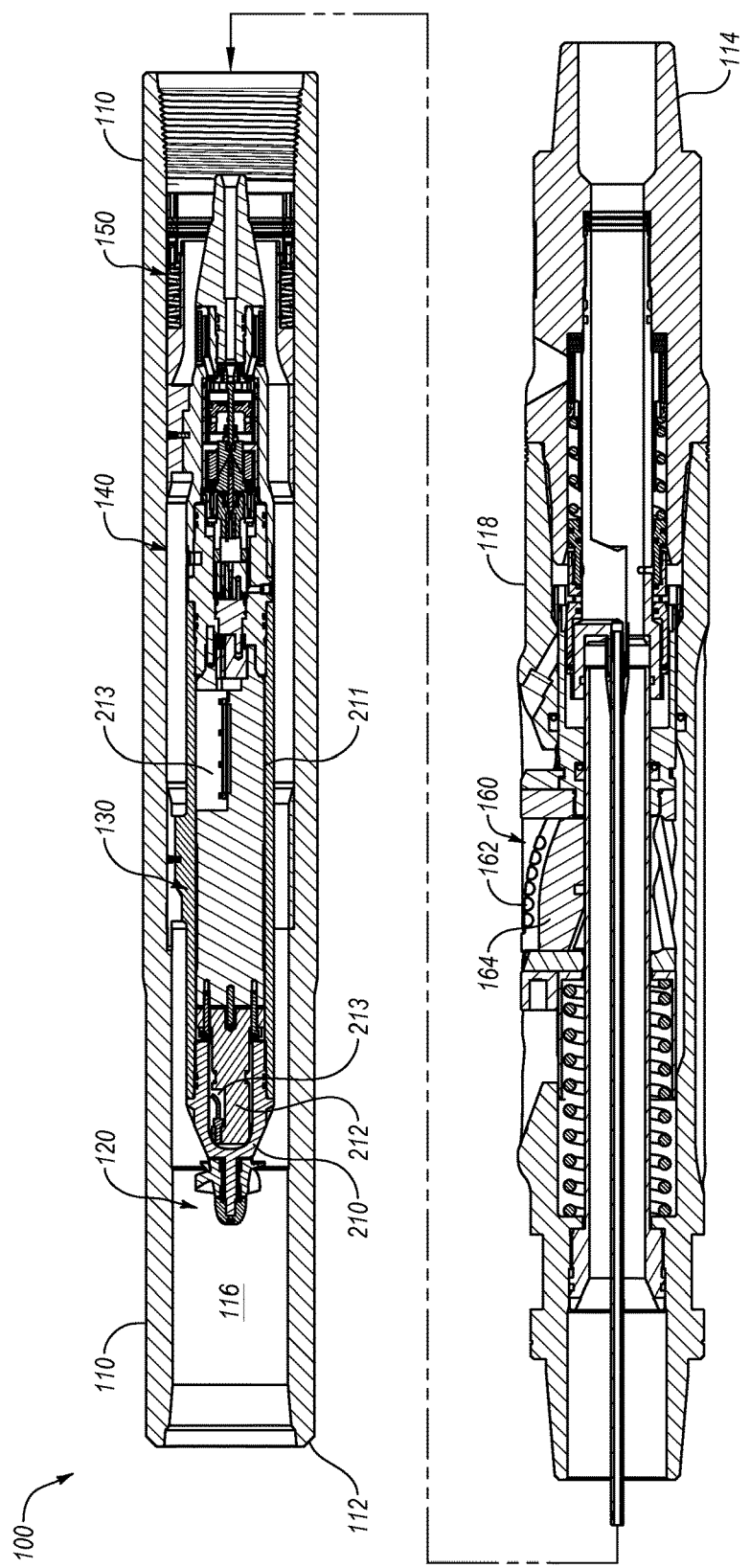
FIG. 1 is a cross-sectional view of an illustrative downhole tool, according to one or more embodiments disclosed herein.

FIG. 1 is a cross-sectional view of an illustrative downhole tool 100, according to one or more embodiments disclosed. The downhole tool 100 may include a body 110 having a first or upper end portion 112 and a second or lower end portion 112. The body 110 may be a single component or two or more components coupled together. In some embodiments, the body 110 may be annular or cylindrical and may have a bore 116 formed axially through a full or partial length thereof.

According to at least some embodiments, the downhole tool 100 may operate as an underreamer, although the downhole tool 100 may be or include any tool that is configured to be run into a wellbore, and may therefore be tools other than underreamers. For example, the downhole tool 100 may be or include a pipe cutter, section mill, bypass valve, bridge plug, whipstock anchor, measurement-while-drilling ("MWD") tool, logging-while-drilling ("LWD") tool, other downhole tools, or any combination of the foregoing.

The downhole tool 100 may include one or more devices configured to actuate between at least two positions. As shown in FIG. 1, such devices may include one or more expandable members (shown here as cutter blocks 160) movably coupled to the body 110. Although a single cutter block 160 is shown, the number of expandable members may vary, and in some embodiments may be between 1 and 20. More particularly, the number of expandable members may be within a range having lower and/or upper limits including any of 1, 2, 3, 4, 5, 7, 9, 12, 15, 18, 20, or any value therebetween. For example, the body 110 may have 3 cutter blocks 160 that are circumferentially-offset from one another. In some embodiments, there may be between 2 and 5 cutter blocks 160 or between 3 and 8 cutter blocks 160. In still other embodiments, there may be more than 20 expandable members.

The downhole tool 100 may be configured to actuate from a first or inactive state (as shown in FIG. 1) to a second or active state. When the downhole tool 100 is in the inactive state, the cutter blocks 160 may be retracted into corresponding recesses in the body 110. In at least one embodiment, when the downhole tool 100 is in the inactive state, the outer radial surfaces 162 of the cutter blocks 160 may be aligned with, or positioned radially-inward from, an outer surface 118 of the body 110. In other embodiments, the outer radial surfaces 162 of the cutter blocks 160 may be positioned slightly radially-outward from the outer surface 118 of the body 110 when the downhole tool 100 is in an inactive state. In such embodiments, the cutter blocks 160 may act as a stabilizer to at least partially stabilize or centralize the body 110 in the wellbore. In some embodiments, a ratio of the radius of the outer radial surfaces 162 of the cutter blocks 160 when in the inactive state relative to the radius of the outer surface 118 of the body 110 (with both being measured from a central longitudinal axis of the body 110) may be from about 0.90:1 to 1.5:1. More particularly, such a ratio may be within a range having lower and/or upper limits including any of 0.9:1, 0.95:1, 0.98:1, 1:1, 1.01:1, 1.02:1, 1.03:1, 1.05:1, 1.1:1, 1.15:1, 1.2:1, 1.25:1, 1.3:1, 1.4:1, 1.5:1, and any values therebetween. For instance, the ratio may be between 0.98 and 1.03:1, between 1.01:1 and 1.05:1, between 1.05:1 and 1.1:1, between 1.1:1 and 1.15:1, or between 1.01:1 and 1.15:1. In other embodiments, the ratio may be less than 0.9:1 or greater than 1.5:1.

The cutter blocks 160 may expand by moving radially outward. In some embodiments, the cutter blocks 160 may move linearly in a radial direction (i.e., perpendicular to a central longitudinal axis of the downhole tool 100). In other embodiments, the cutter blocks 160 may pivot and follow a curved path to expand. In yet other embodiments, the cutter blocks 160 may move in both longitudinal and radial directions to expand along a path that is linear, curved, or has portions that include any combination of linear or curved paths.

In the particular embodiment shown in FIG. 1, the cutter blocks 160 may have a plurality of splines 164 formed on the outer side surfaces thereof. The splines 164 may be or include offset ridges or protrusions configured to engage corresponding grooves in the body 110. The splines 164 on the cutter blocks 160 (and the corresponding grooves) may be oriented at an angle with respect to a central longitudinal axis through the body 110. In some embodiments, the angle may be between 5° and 60°. More particularly, the splines 164 and/or grooves may be at an angle that is within a range having lower and upper limits that include any of 5°, 10°, 15°, 17°, 20°, 23°, 25°, 30°, 35°, 40°, 45°, 60° and any values therebetween. For instance, the angle may be between 15° and 25°, or between 17° and 23°. In still other embodiments, the angle may be less than 5° or greater than 60°.

When the downhole tool 100 actuates from the inactive state to the active state, the engagement of the splines 164 on the cutter blocks 160 and the grooves in the body 110, in combination with hydraulic or other forces, may cause the cutter blocks 160 to move axially or longitudinally toward the first end portion 112 of the body 110, while simultaneously moving radially outward. The resultant movement may be at the angle similar to the angle at which the splines 164 are oriented (e.g., between 5° and 60° with respect to the central longitudinal axis through the body 110).

When the downhole tool 100 is in the active state, the outer radial surfaces 162 of the cutter blocks 160 may be positioned radially outward from the outer surface 118 of the body 110. When the downhole tool 100 is in the active state, a ratio of the radius of the outer radial surfaces 162 of the cutter blocks 160 to the radius of the outer surface 118 of the body 110 may be between 1:05:1 and 1.95:1. More particularly, the ratio may be within a range having lower and/or upper limits that include any of 1.05:1, 1.1:1, 1.15:1, 1.2:1, 1.25:1, 1.3:1, 1.35:1, 1.4:1, 1.5:1, 1.6:1, 1.7:1, 1.8:1, 1.9:1, 1.95:1, and any values therebetween. For instance, the ratio may be between 1.1:1 and 1.2:1, between 1.15:1 and 1.25:1, between 1.2:1 and 1.3:1, between 1.25:1 and 1.35:1, or between 1.3:1 and 1.4:1. In other embodiments, the ratio may be less than 1.05:1 or greater than 1.95:1.

The cutter blocks 160 may each have a plurality of cutting contacts or elements on, in, or otherwise coupled to the outer radial surfaces 162 thereof. The cutting elements of the cutter blocks 160 may be made superhard or superabrasive materials (e.g., tungsten carbide, cobalt-cemented tungsten carbide, titanium carbide, niobium carbide, polycrystalline diamond, cubic boron nitride, etc.). The cutting elements on the cutter blocks 160 may cut, grind, shear, crush, or otherwise deform a wall of the wellbore, thereby increasing the diameter of the wellbore when the downhole tool 100 is in the active state. The cutter blocks 160 may also include one or more stabilizer pads 161 on the outer radial surfaces 162 thereof.

A sensor assembly 120, a power source 130, an electronics assembly 140, an actuator assembly 150, or some combination of the foregoing, may be coupled to the body 110. In FIG. 1, for instance each of the sensor assembly 120, power source 130, electronics assembly 140, and actuator assembly 150 may be at least partially within the bore 116 of the body 110. The sensor assembly 120 may be positioned proximate the first end portion 112 of the body 110 or the second end portion 112 of the body 110. As shown, the sensor assembly 120 may be positioned between the first end portion 112 of the body 110 and the power source 130, the electronics assembly 140, and the actuator assembly 150. The sensor assembly 120 may be configured to sense or measure one or more properties of a fluid flowing through the bore 116. In some embodiments, the sensor assembly 120 may be used in an actuation mechanism for the downhole tool 100. Example embodiments of a sensor assembly 120 are discussed in greater detail herein (e.g., with respect to FIGS. 2-8).

The power source 130 may provide power to the sensor assembly 120, the electronics assembly 140, the actuator assembly 150, or some combination of the foregoing. The power source 130 may be or include one or more batteries, a turbo-generator, or other examples. The electronics assembly 140 may receive and interpret (e.g., decode) one or more signals from the sensor assembly 120. In some embodiments, the received signals may represent or include one or more properties of the fluid in the bore 116. In response to the one or more signals, the electronics assembly 140 may transmit a signal to the actuator assembly 150. According to some embodiments, the transmitted signal may be a control signal to allow the electronics assembly 140 to control the actuator assembly 150. For example, the electronics assembly 140 may cause the actuator assembly 150 to expand or retract the cutter blocks 160 (e.g., by opening a valve to allow fluid to actuate the cutter blocks 160).

Figure 2:
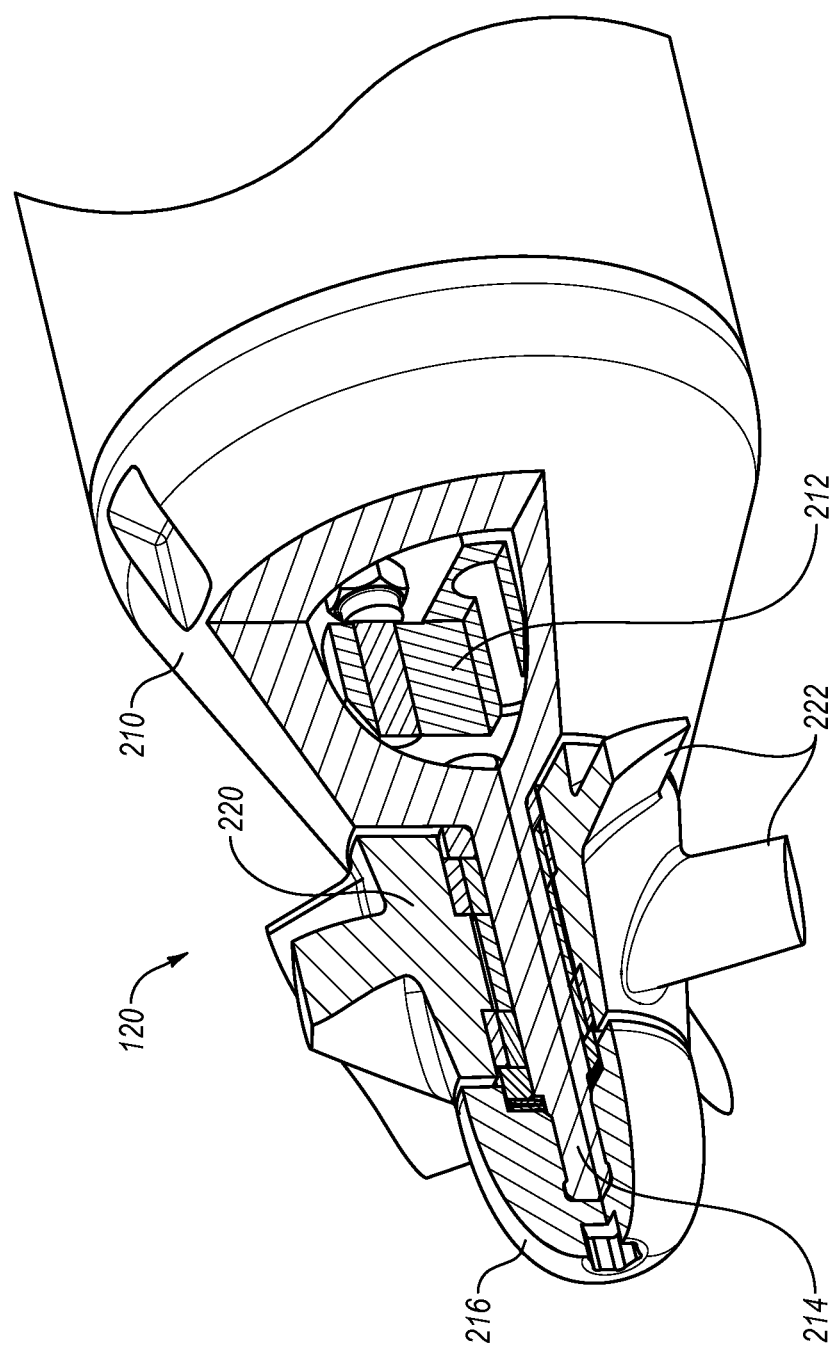
FIG. 2 is a partial cross-sectional view of an illustrative sensor assembly of a downhole tool, according to one or more embodiments disclosed herein.

FIG. 2 is a partial cross-sectional view of the sensor assembly 120 shown in FIG. 1, according to one or more embodiments. Referring to FIGS. 1 and 2, the sensor assembly 120 may include a sensor housing 210 defining an optional atmospheric chamber 212. The sensor housing 210, either alone or in combination with a tubular housing 211, may be configured to maintain the atmospheric chamber 212, at or near atmospheric pressure (e.g., from 80 kPa to 120 kPa) even when the pressure of fluid in the bore 116 may be higher (e.g., greater than 0.25 MPa, 0.5 MPa, 1 MPa, 2 MPa, 5 MPa, 10 MPa, 50 MPa, 100 MPa, 200 MPa, or even higher). In other embodiments, the atmospheric chamber 212 may be maintained at a reference pressure other than atmospheric pressure.

A rod or shaft 214 may be integral with, or otherwise coupled to, the sensor housing 210 and may extend longitudinally outward from the sensor housing 210. In some embodiments, an impeller 220 may be coupled to the shaft 214. The impeller 22 may be positioned around at least a portion of the shaft 214, and configured to rotate thereabout. The impeller 220 may include one or more blades 222 that extend radially outward therefrom. The blades 222 may be circumferentially offset from one another with respect to a central longitudinal axis extending through the shaft 214 and/or the impeller 220. The blades 220 may be curved, straight, or include combinations of curved and straight sections. In some embodiments, leading edges of the blades 220 may be inclined (e.g., swept backwards), which may reduce or even prevent the accumulation of flakes or fibers on the leading edges.

The impeller 220 may rotate in response to the fluid flowing through the bore 116, as discussed in greater detail herein. In at least one embodiment, the impeller 220 may be a pump, or may include a pump, which may be driven by a motor. In other embodiments, the impeller 220 may include a turbine that drives a generator. A lock nut 216 may be coupled (e.g., threaded) to the shaft 214 to secure the impeller 220 axially/longitudinally between the lock nut 216 and the housing 210. The impeller 220 may rotate independent of the shaft 214, or the impeller 220 may cause the shaft 214 to rotate.

Figure 3:
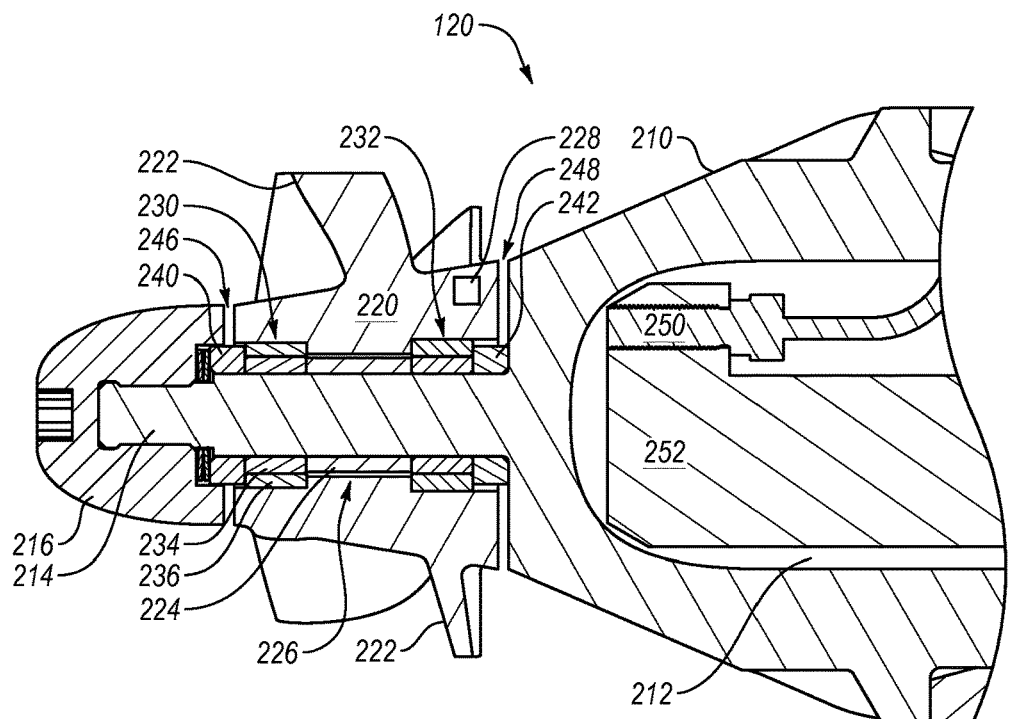
FIG. 3 is a cross-sectional view of the sensor assembly shown in FIG. 2, according to one or more embodiments disclosed herein.

FIG. 3 is a cross-sectional view of the sensor assembly 120 of FIG. 2, according to one or more embodiments. One or more bearings (four bearings 230, 232, 240, 242 are illustrated) may be coupled to the shaft 214 and/or the impeller 220. In FIG. 3, for instance, the bearings 230, 232, 240, 242 are shown as being positioned around the shaft 214. As shown, two of the bearings (i.e., bearings 230, 232) may be journal bearings and/or may be positioned at least partially between the shaft 214 and the impeller 220. Each of the bearings 230, 232 may include an inner sleeve 234 and an outer sleeve 236. The inner sleeves 234 may be stationary with respect to the shaft 214, and the outer sleeves 236 may be stationary with respect to the impeller 220. As such, the impeller 220 and the outer sleeves 236 may be configured to rotate with respect to the shaft 214 and inner sleeves 234, either or both of which may remain stationary or may rotate at a different speed than the impeller 220.

In some embodiments, a radial clearance between the outer diameter of the inner sleeves 234 and the inner diameter of the outer sleeves 234 may be between 1 μm and 1 mm. In some embodiments, the radial clearance may be up to 1 mm, up to 100 μm, up to 25 μm, up to 10 μm, up to 1 μm, or even greater than 1 mm. This radial clearance may limit the amount and/or size of particles in the fluid that may flow through the bearings 230, 232, thereby restricting or even preventing the accumulation of particles in and/or around the bearings 230, 232. This radial clearance may further reduce friction in the bearings 230, 232 and allow, in some embodiments, for a linear or other response of the flow measurement by the sensor assembly 120, as discussed herein.

In some embodiments, a first spacer 224 may be positioned axially between the inner sleeves 234 of the bearings 230, 232, and a second spacer 226 may be positioned axially between the outer sleeves 236 of the bearings 230, 232. The first spacer 224 may not rotate, or may rotate at a different speed with respect to the impeller 220. The second spacer 226 may be integral with, or otherwise coupled to, the impeller 220 and configured to rotate therewith. In other embodiments, at least one of the first or second spacers 224, 226 may be omitted, the first spacer 224 may rotate with the impeller 220, or the second spacer 226 may rotate at a different speed than the impeller 220.

In FIG. 3, two additional bearings (i.e., bearings 240, 242) may be thrust bearings. The bearings 240, 242 may be located at least partially around the shaft 214. One bearing 240 may be positioned axially between the lock nut 216 and the bearings 230, 232, while the second bearing 242 may be positioned axially between the bearings 230, 232 and the housing 210. When used as thrust bearings, the bearings 240, 242 may be configured to support an axial load generated upon the impeller 220 by the fluid flowing through the bore 116. For example, the bearing 240 may support the axial load generated upon the impeller 220 by a "reverse" flow in the bore 116 (e.g., right to left in FIG. 3), and the bearing 242 may support the axial load placed upon the impeller 220 by a "forward" flow in the bore 116 (e.g., left to right in FIG. 3). A variety of configurations of one or more bearings 230, 232, 240, 242 are contemplated for supporting the impeller 220 against axial loads. Further, in certain embodiments, the functions of the bearings 230, 232 (e.g., journal bearings) and the bearings 240, 242 (e.g., thrust bearings) may be provided by combined thrust and journal bearings. As shown in FIG. 3, an axial load on the impeller 220 may be transmitted by a flat surface of the bearing 232 onto a flat surface of the bearing 242. These surfaces may slide on each other (e.g., move radially relative to each other) when the impeller 220 is turning.

As the lock nut 216 is tightened, the bearings 240, 242, the inner sleeves 234 of the bearings 230, 232 and the first spacer 224 may be axially compressed between the lock nut 216 and the sensor housing 210. This may restrict or even prevent these components from rotating relative to the shaft 214 (but they may rotate with the shaft 214). In addition, one or more flats or keyed surfaces may be integral with, or otherwise coupled to, the bearings 240, 242, the inner sleeves 234 of the bearings 230, 232, or the first spacer 224. The flats or other keyed surfaces may be configured to engage with corresponding surfaces on the shaft 214 to further restrict or even prevent relative rotation therebetween. In other embodiments, splines, dovetails, mechanical interlocks, or other features may be used to restrict relative rotation.

Once the lock nut 216 is tightened on the shaft 214, a first axial gap 246 may exist between the lock nut 216 and the impeller 220. A second axial gap 248 may exist between the impeller 220 and the housing 210. The gaps 246, 248 may allow the impeller 220 to rotate without frictional forces caused by contacting the lock nut 216 and/or the housing 210, or with reduced frictional forces due to contact with the lock nut 216 and/or the housing 210.

At least a portion of the bearings 230, 232 and/or the bearings 240, 242 may be made from, or at least partially include, polycrystalline diamond, tungsten carbide, ceramic, stellite, other similar materials, or a combination of the foregoing. For example, the inner and/or outer sleeves 234, 236 of the bearings 230, 232 may be made from polycrystalline diamond material. The polycrystalline diamond material may be leached to at least partially remove cobalt (and any other metals or binders) therefrom. This may reduce friction within the bearings 230, 232, 240, 242 and improve the measurement quality of the sensor assembly 120.

The bearings 230, 232, 240, 242 may be designed and arranged, or otherwise configured, to minimize the amount of fluid maintained between the surfaces of the bearings 230, 232, 240, 242. To achieve this, one or more surfaces in the bearings 230, 232, 240, 242 may have grooves or other fluid pathways formed therein. The fluid in the grooves may reduce or prevent the bearings 230, 232, 240, 242 from sticking (e.g., when the impeller 220 begins to rotate from a stationary position).

The impeller 220 may include one or more markers to allow the position of the impeller 220 to be detected. The markers may be or include a magnetized portion (e.g., a locally magnetized portion and/or one or more magnets 228 coupled to the impeller 220). As shown, a magnet 228 may be coupled to one of the blades 222 of the impeller 220. In another embodiment, the markers may include one or more recesses or cavities in the impeller 220. One or more sensors 250 (e.g., position sensors, material sensors, proximity sensors, etc.) may be within the atmospheric chamber 212 of the sensor housing 210 and tubular housing 211 and/or proximate the impeller 220 or magnet 228. A sensor 250 should be considered proximate the impeller 220 or magnet 228 when separated by less than or equal to 10 cm, less than or equal to 5 cm, less than or equal to 2 cm, less than or equal to 1 cm, less than or equal to 500 mm, less than or equal to 100 mm, less than or equal to 50 mm, less than or equal to 1 mm, or less than or equal to 500 μm. In other embodiments, the sensor 250 may be installed outside the sensor housing 210 and in contact with the fluid. As shown, a sensor 250 may be within the chamber 212 and threaded into a chassis 252 in the sensor housing 210. The sensor 250 may be an induction coil, a Hall Effect sensor, or a magnetoresistive sensor. The sensor 250 may be installed inside the sensor housing 210 and detect magnetic properties or magnetic effects generated by the impeller 220. The sensor housing 210 may be made from a non-magnetic material to allow the transmission of the magnetic effect across the sensor housing 210. In another embodiment, no magnets 228 may be coupled to the impeller 220, and the sensor 250 may be a variable reluctance sensor.

In some embodiments, the magnet 228 and the sensor 250 may be substantially the same distance from the central longitudinal axis of the sensor assembly 120 (i.e., radially-aligned). Fluid flowing through the bore 116 may cause the impeller 220 and the magnet 228 to rotate about the shaft 214. The sensor 250 may be configured to sense or measure when the magnet 228 passes thereby. More particularly, the magnet 228 may induce a voltage in the sensor 250 each time the rotating magnet 228 passes thereby. In some embodiments, the chassis 252 may be made of a non-magnetic material so as to not interfere with the sensing of the magnet 228.

The sensor assembly 120 may transmit one or more signals to the electronics assembly 140 indicating the rate of rotation (e.g., in revolutions per minute, revolutions per second, radians per second, etc.) of the impeller 220. The electronics assembly 140 may determine the flow rate of the fluid through the bore 116 based at least partially on the rate of rotation (i.e., rotational velocity or rotational speed) of the impeller 220. For example, a faster rotation of the impeller 220 indicates a higher the flow rate in the bore 116 and a faster the velocity of the fluid in the bore 116. The rotational velocity of the impeller 220 may increase substantially linearly with the flow rate. This linear behavior may apply for at least some levels of viscosity. In the linear region of operation, the flow rate may be determined from the rotational velocity by flow modeling around the impeller 220 and sensor flow calibration.

Figure 4:
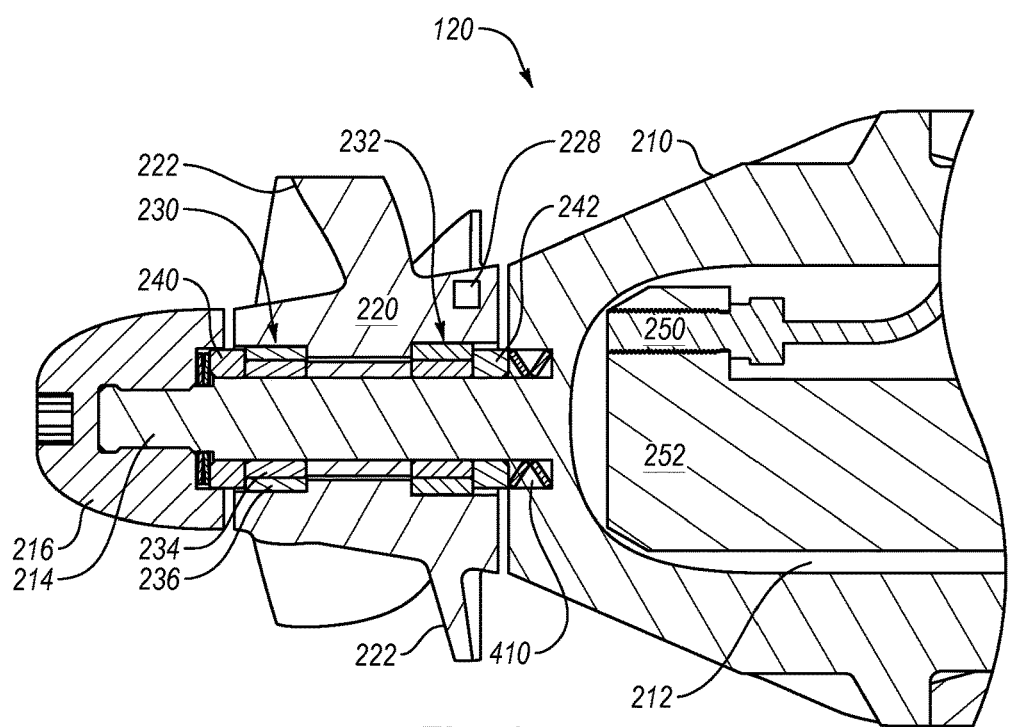
FIG. 4 is a cross-sectional view of the sensor assembly shown in FIGS. 2 and 3 with a thrust spring, according to one or more embodiments disclosed herein.

FIG. 4 is a cross-sectional view of the sensor assembly 120 shown in FIGS. 2 and 3 with a biasing element (e.g., a thrust spring 410), according to one or more embodiments. The thrust spring 410 may be at least partially located around the shaft 214 and/or axially between the impeller 220 and the sensor housing 210. The thrust spring 410 may be positioned between the bearing 232 (i.e., a second journal bearing) and the housing 210 and/or between the bearing 242 (i.e., a second thrust bearing) and the housing 210.

A "forward" flow of fluid in the bore 116 (from left to right in FIG. 4) may generate a hydraulic drag force on the impeller 220, and the thrust spring 410 may allow the impeller 220 to move axially along the shaft 214 (to the right in FIG. 4) when the drag force exceeds the opposing spring force. This may reduce the axial distance between the magnet 228 and the sensor 250. The sensor 250 may be able to sense or measure this variation in axial distance, and the variation may be reflected as a variation (e.g., increase) in the amplitude of the signal from the sensor 250. Other detection methods may be used to determine the change of axial position of the impeller 220. For example, the force generated in the thrust spring 410 may be measured using a force sensor in contact with the thrust spring 410. In another embodiment, a linear variable differential transformer (LVDT) may be used to measure the displacement of the thrust bearing 242 or the impeller 220.

The one or more signals transmitted from the sensor assembly 120 to the electronics assembly 140 (FIG. 1) may also include the axial movement and/or position of the impeller 220. The electronics assembly 140 may determine the drag force on the impeller 220 based at least partially on the axial distance that the impeller 220 moves and the spring coefficient of the thrust spring 410. At least a portion (e.g., a majority) of the drag force may be generated by the viscous effect of the fluid. In some embodiments, the density of the fluid in the bore 116 may have a minimal effect on the drag force.

Figures 2, 5:
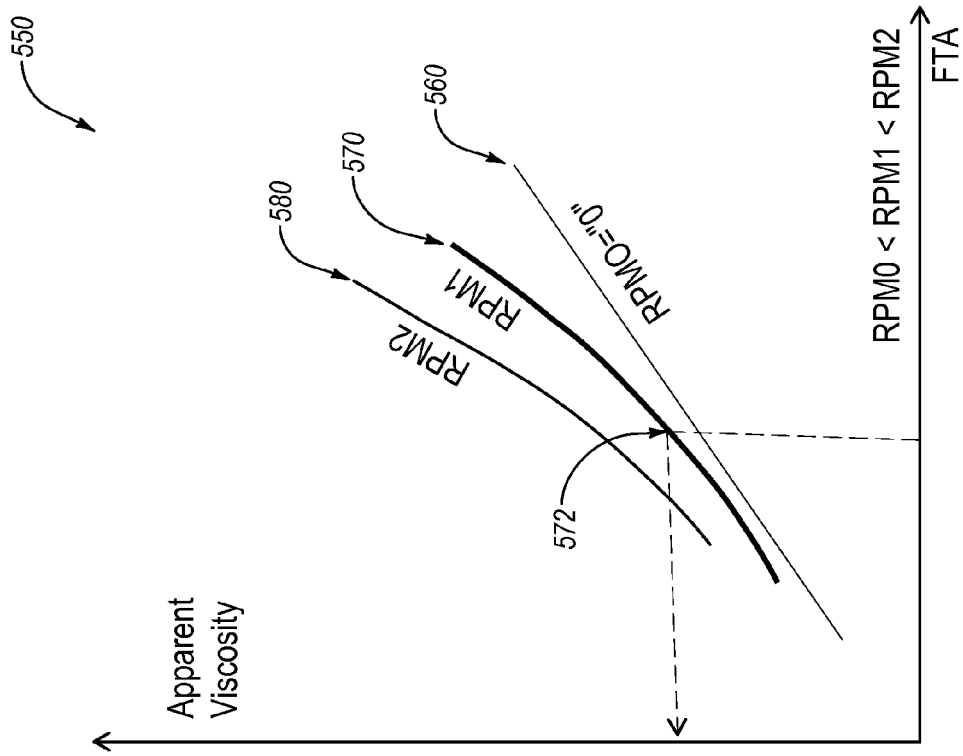
Figures 1, 5:
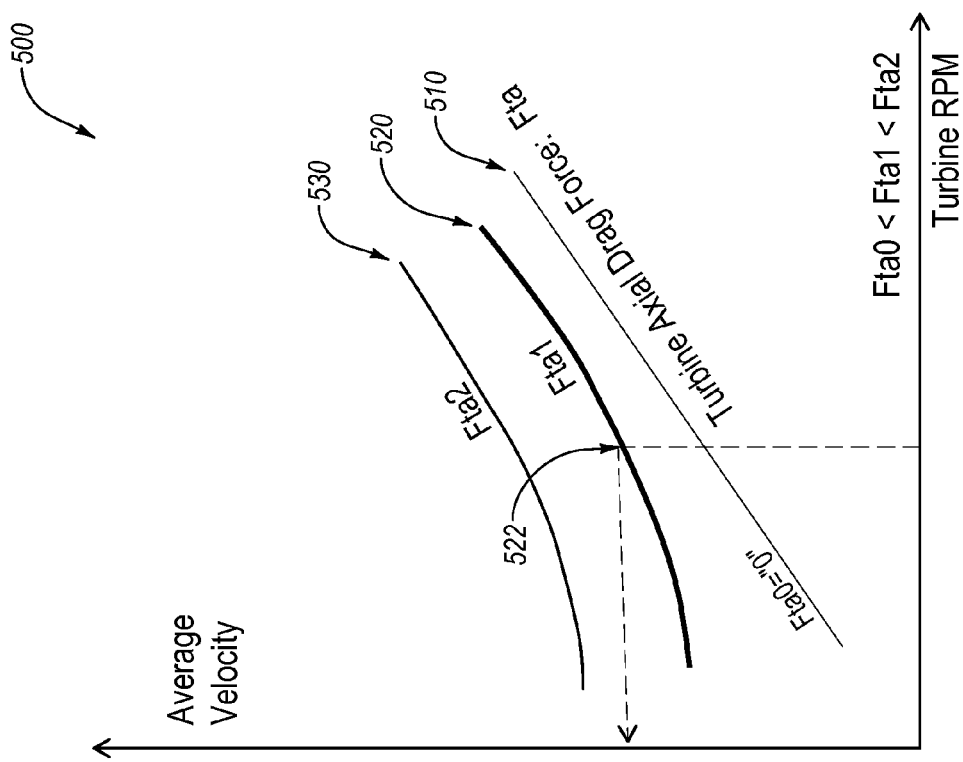

FIGS. 5-1 and 5-2 depict illustrative calibration charts 500, 550 for use in determining the average velocity of fluid and the apparent viscosity of the fluid, respectively, according to one or more embodiments. The average velocity of the fluid and/or the apparent viscosity of the fluid may be determined using the rate of rotation of an impeller (e.g., impeller 220 of FIG. 4), the axial drag force on an impeller, or a combination thereof. In at least one embodiment, the average velocity of the fluid and/or the apparent viscosity of the fluid may be determined using an illustrative lookup table, which may be represented by the charts 500, 550. FIG. 5-1 shows three illustrative curves 510, 520, 530 representing the drag force on an impeller. By identifying a point (e.g., point 522) on a particular drag force curve (e.g., curve 520) that lines up with a selected rotational velocity, the average velocity of the fluid flowing past the impeller may be determined. For example, the average velocity may be used with (e.g., multiplied by) the area of the flow passage in the section of the impeller, and the flow rate may be determined with no (or low) dependence on fluid viscosity. This may make the flow measurement more accurate over a wider range of flows and over a wider range of fluid viscosities.

FIG. 5-2 shows three illustrative curves 560, 570, 580 representing the rotational velocity of an impeller. By identifying a point (e.g., point 572) on a particular rotational velocity curve (e.g., curve 570) that lines up with a selected axial drag force, the average velocity of the fluid flowing past the impeller may be determined. This may allow the determination of the apparent viscosity corresponding to a measured axial drag force, after selection of the proper curve corresponding to the turbine rotational velocity.

The shape of an impeller may be modified or optimized to increase the axial drag force on the impeller. This may be achieved by increasing the length of the blades. In other embodiments, a shroud (see FIG. 8) may be added to or beyond the outer radial edges of the blades to further increase the axial drag force.

Figures 2, 6:
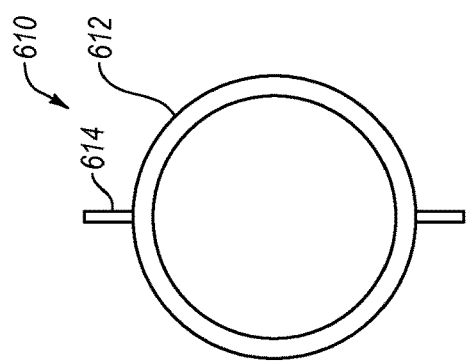
Figures 1, 6:
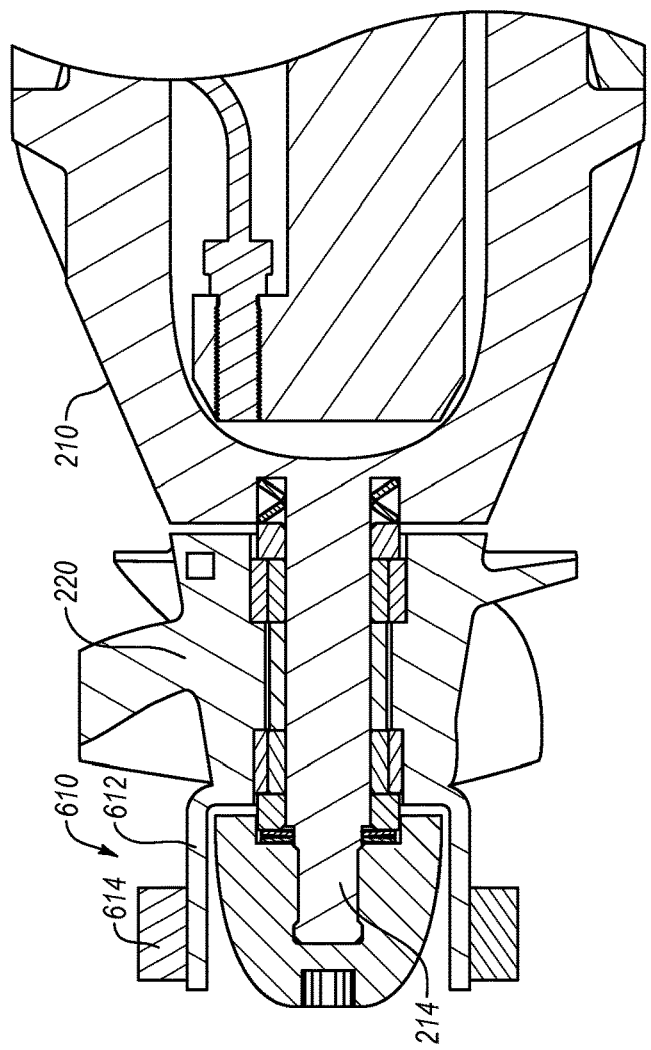
Figures 3, 6:
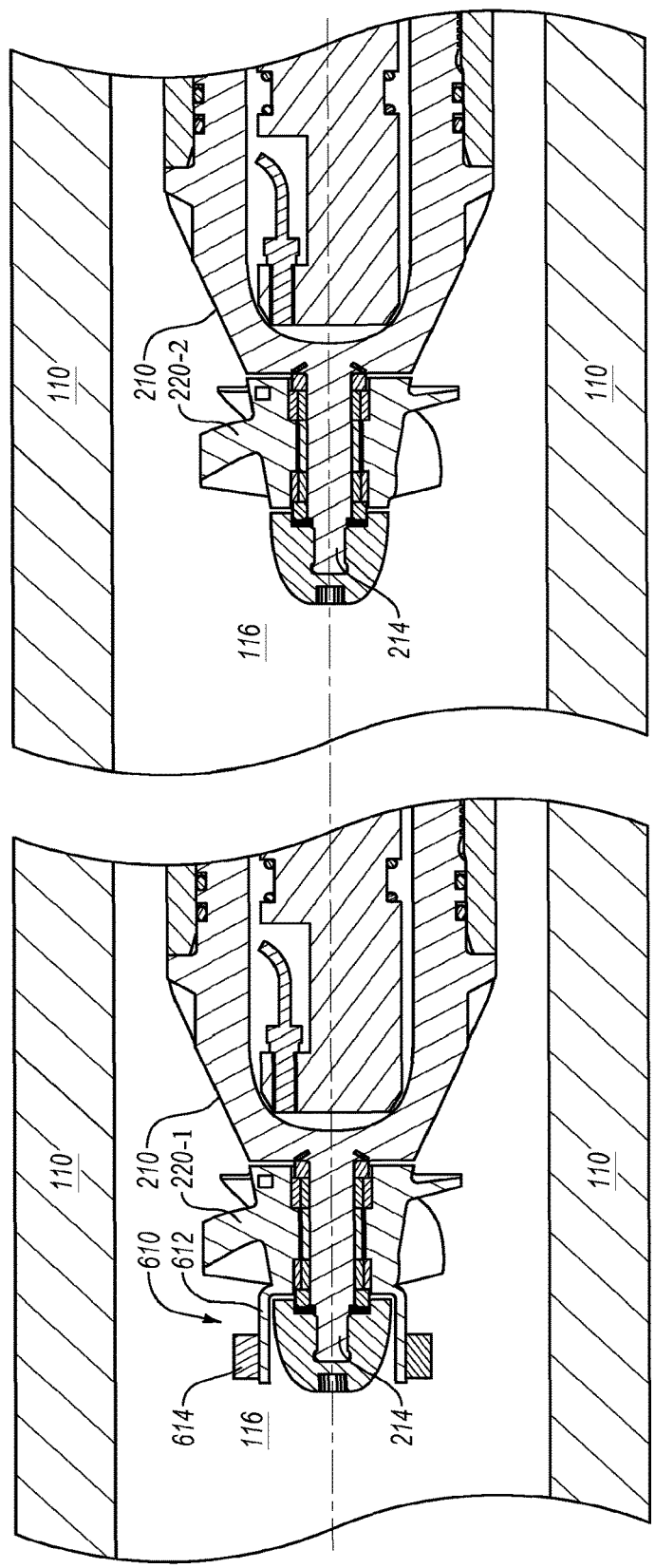

FIG. 6-1 is a cross-sectional view of the sensor assembly 120 shown in FIGS. 2 and 3 with a brake 610, and FIG. 6-2 is a front end view of the brake 610, according to one or more embodiments. The brake 610 may be coupled to the impeller 220 and optionally configured to rotate therewith. The brake 610 may be or include an annular body 612 that may be positioned at least partially around the lock nut 216 and/or the impeller 220. One or more fins 614 (two are shown) may extend radially outward from the body 612. In some embodiments, the fins 614 extend axially and substantially parallel to a central longitudinal axis extending through the brake 610 and/or the shaft 214. In some embodiments, the fins 614 may further extend radially in a direction substantially perpendicular to the central longitudinal axis. In some embodiments, the fins 614 may extend axially or radially at angles relative to the central longitudinal axis, may be curved, or may have other configurations.

The fins 614 may increase the torque on the impeller 220 as the impeller 220 rotates, thereby decreasing the rate of rotation of the impeller 220. A change in the rate of rotation may be at least partially dependent upon the density of the fluid. The rate of rotation of the impeller 220 and/or the axial drag force on the impeller 220 may be measured (e.g., using the sensor assembly 120) with and/or without the brake 610 coupled to the impeller 220. The one or more signals transmitted from the sensor assembly 120 to the electronics assembly 140 may include such measurements. The electronics assembly 140 may determine the difference between the rate of rotation of the impeller 220 with and without the brake 610 and/or the axial drag force on the impeller 220 with and without the brake 610.

The measurements with and without the brake 610 may be obtained in several different ways. In at least one embodiment, two impellers 220 may be axially-offset from one another in the bore 116, with one having a brake 610 coupled thereto and one not having a brake 610 coupled thereto. This may enable the measurements to be taken continuously and/or simultaneously. The impellers 220 in this example may not, however, have the same "response" because the impellers 220 may not be mounted in the same way in the bore 116. In addition, the upstream impeller 220 may affect the flow passing through the downstream impeller 220.

In another embodiment, the brake 610 may be coupled to and decoupled from a single impeller 220. The coupling and decoupling of the brake 610 may be controlled, for example, by a controller, electromagnet, or the like. The time intervals with and without the brake 610 may range from 0.5 second to 10 minutes. For instance, the time intervals may range from 5 seconds to 30 seconds, from 10 seconds to 1 minute, or from 30 seconds to 5 minutes. In other embodiments, the time interval may be less than 2 seconds or more than 10 minutes. In some embodiments, the measurements may be taken near the end of the time intervals to allow the impeller 220 to reach steady state conditions.

FIG. 6-3 is a cross-sectional view of a downhole tool including two sensor assemblies, each of which may include an impeller 220-1, 220-2. The impellers 220-1, 220-2 may be axially offset from one another in the bore 116, with a first impeller 220-1 having a brake 610 coupled thereto and the second impeller 220-2 not having a brake 610 coupled thereto. The illustrated arrangement may allow the impellers 220-1, 220-2 to take continuous and/or simultaneous measurements (e.g., to compare measurements obtained by the impellers 220-1, 220-2). In some embodiments, the impellers 220-1, 220-2 in this example may not, however, have the same "response." For instance, the impellers 220-1, 220-2 may not be mounted in the same way in the bore 116, thereby varying their respective responses. In addition, the first impeller 220-1 (which may be an uphole or upstream impeller) may affect the flow passing to the second impeller 220-2 (which may be a downhole or downstream impeller).

Figures 2, 7:
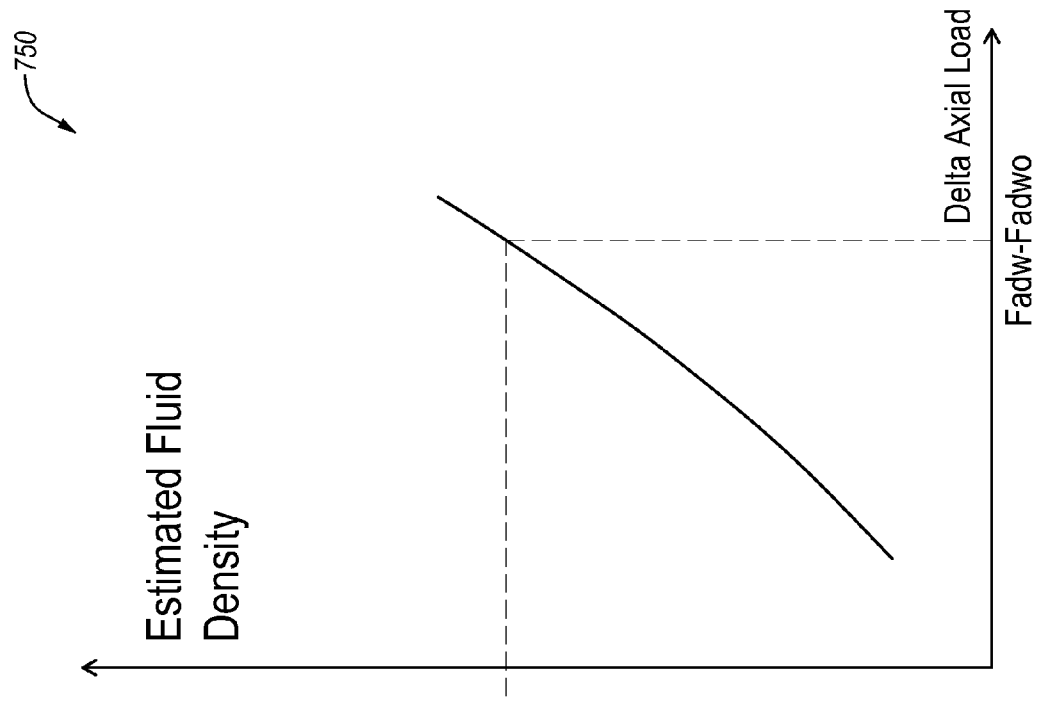
Figures 1, 7:
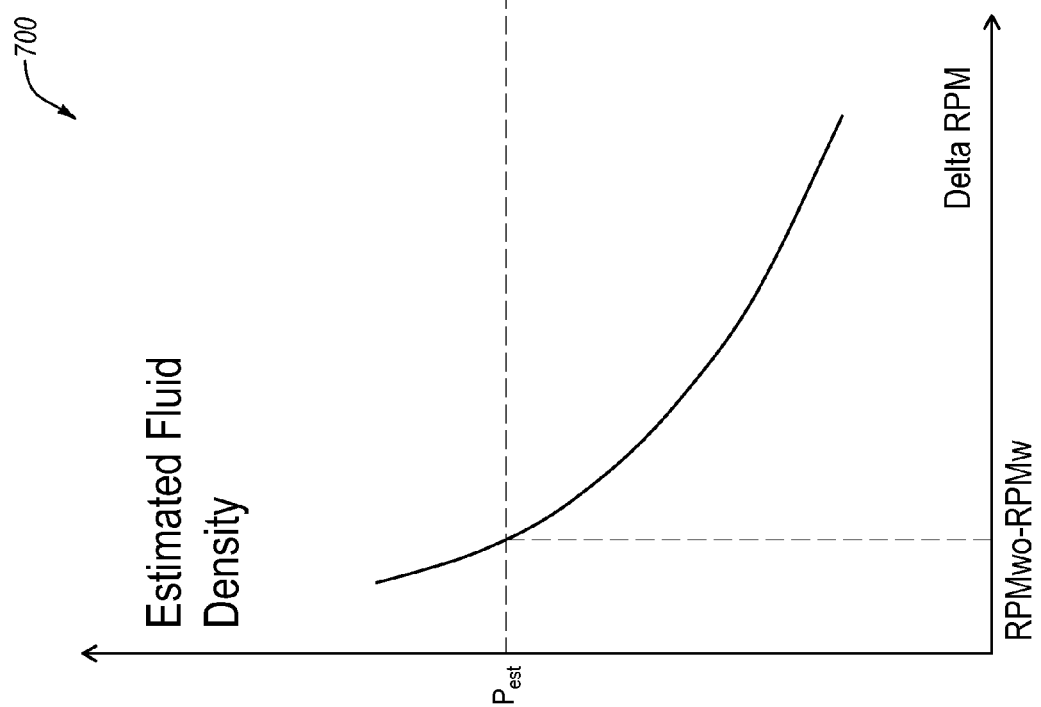

FIG. 7-1 is an illustrative graph 700 showing an estimated density of fluid based on a difference between a rate of rotation of a first impeller (e.g., impeller 220) with and without a brake (e.g., brake 610), according to one or more embodiments. FIG. 7-2 is an illustrative graph 750 showing the estimated density of fluid based on the difference between axial drag force on an impeller of the present disclosure with and without a brake, according to one or more embodiments. An electronics assembly (e.g., electronics assembly 140 of FIG. 1) may determine the density of the fluid in a bore (e.g., bore 116) based at least partially on the difference between the rate of rotation of the impeller with and without the brake and/or the difference between axial drag force on the impeller with and without the brake.

An electronics assembly may, for example, determine (e.g., compute or look-up) the density of the fluid using one or both of the graphs 700, 750. The graph 700 of FIG. 7-1 includes the difference between the rate of rotation of an impeller with and without a brake along the X-axis, and the estimated density of the fluid on the Y-axis. The graph 750 of FIG. 7-2 includes the difference between axial drag force on an impeller with and without the brake 610 along the X-axis, and the estimated density of the fluid on the Y-axis. In some embodiments, the estimated densities from the graphs 700, 750 may be combined or averaged to determine the density of the fluid.

Figure 8:
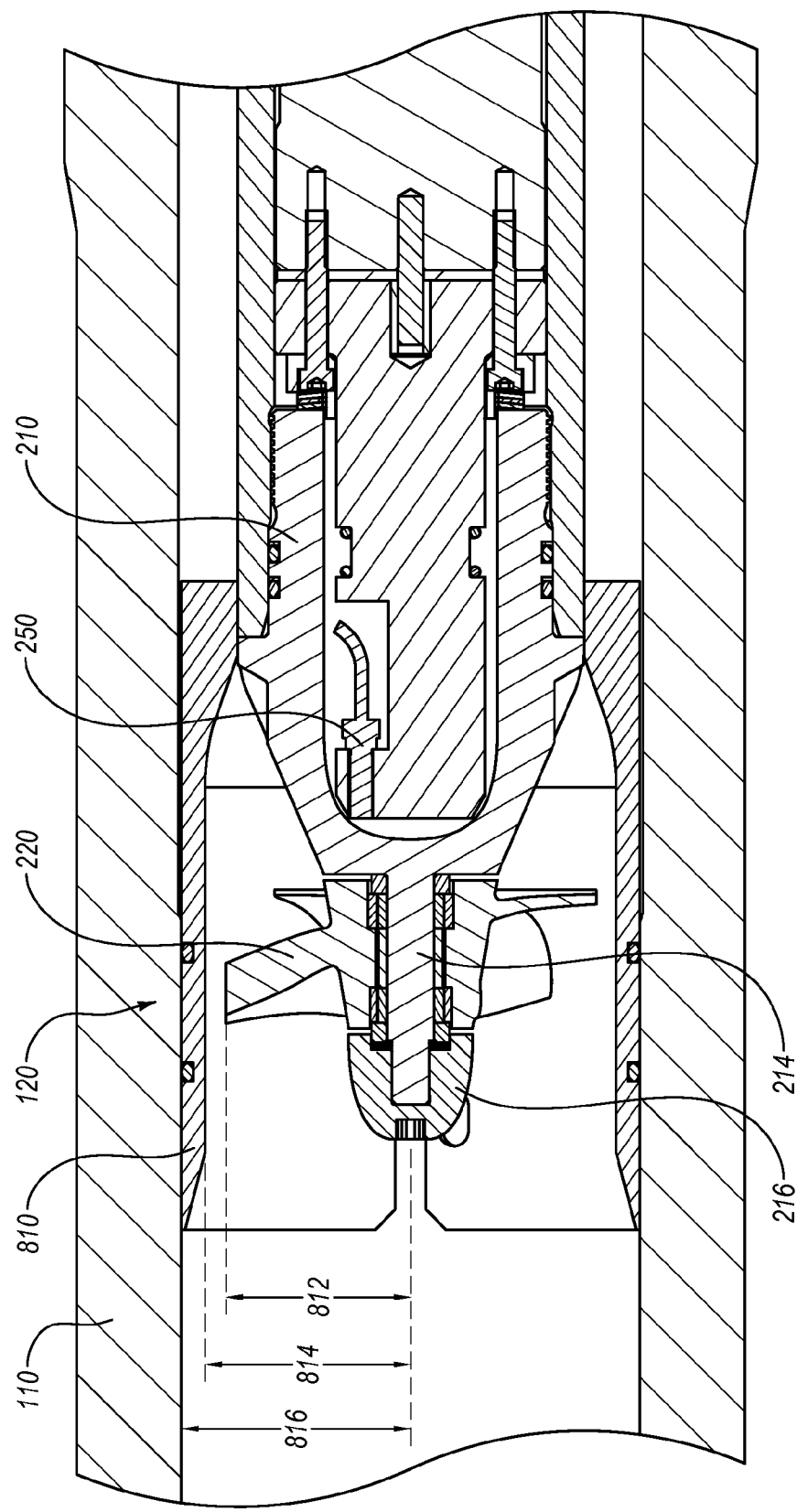
FIG. 8 is a cross-sectional view of the sensor assembly shown in FIGS. 2 and 3 with a shroud at least partially around the sensor assembly, according to one or more embodiments disclosed herein.

FIG. 8 is a cross-sectional view of the sensor assembly 120 shown in FIGS. 2 and 3 with a shroud 810 at least partially therearound, according to one or more embodiments. The shroud 810 may be positioned radially around the impeller 220, and radially between the impeller 220 and an inner surface of the body 110. According to at least some embodiments, the shroud 810 may focus a flow of fluid by reducing the radial gap through which particles in the fluid pass around the impeller 220. A ratio of the radius 812 of the impeller 220 to the radius 814 of the inner surface of the shroud 810 may be from 0.3:1 to 1:1 in some embodiments. For instance, the ratio may be between 0.5:1 and 0.85:1, between 0.8:1 and 0.99:1, between 0.9:1 and 0.99:1, or between 0.95:1 and 0.99:1. In other embodiments, the ratio may be less than 0.3:1.

In some embodiments, the shroud 810 may be omitted, thereby providing a larger radial gap through which particles in the fluid may flow. With the shroud 810 omitted, a ratio of the radius 812 of the impeller 220 to the radius 816 of the inner surface of the body 110 may be from 0.2:1 to 0.95:1. For instance, the ratio may be between 0.35:1 and 0.85:1, between 0.5:1 and 0.9:1, between 0.6:1 and 0.85:1, between 0.7:1 and 0.9:1, or between 0.8:1 and 0.95:1. In other embodiments, the ratio may be less than 0.2:1 or greater than 0.95:1.

In operation, a downhole tool of the present disclosure (e.g., downhole tool 100) may be run into a wellbore on a drill string that includes drill pipe, drill collars, coiled tubing, production tubing, wireline, slickline, other components, or any combination of the foregoing. Fluid may flow through the wellbore. For instance, a pump at the surface may cause the fluid to flow through the interior of a drill string (e.g., through drill pipe, coiled tubing, or other tubing string) and to flow to the bore 116 of the downhole tool 100 and/or through an annulus formed between the downhole tool 100 and the wall of the wellbore.

The fluid may be or include water, drilling mud (e.g., aerated mud), cement slurry, well treatment fluids (e.g., stimulation fluids and/or foaming fluids), other fluids, or any combination of the foregoing. In some embodiments, the fluid may have particles dispersed therein. For example, in drilling mud, the particles may be or include barite, hematite, flake lost-circulation material (LCM), crushed nut shell LCM, crushed carbonate, other particles, or any combination of the foregoing. In cement slurry, the particles may be or include cement particles. In stimulation fluid, the particles may be or include ceramic or other proppant materials. In the same or other embodiments, sand and/or metallic particles may be present in the fluid. At least some of the particles may have an average cross-sectional length (e.g., diameter) between 0.05 mm and 20 mm. For instance, the average cross-sectional length may be between 0.1 mm and 1 mm, between 1 mm and 5 mm, or between 5 mm and 10 mm. In other embodiments, the average cross-sectional length may be less than 0.05 mm or greater than 20 mm.

Fluid pumped into a drill string may have a pressure between 0.5 MPa and 1,000 MPa in some embodiments. For instance, the fluid pressure may be between 1 MPa and 10 MPa, between 10 MPa and 50 MPa, between 50 MPa and 100 MPa, between 100 MPa and 200 MPa, or between 200 MPa and 500 MPa. In other embodiments, the fluid pressure may be less than 0.5 MPa or greater than 1,000 MPa. In some embodiments, the fluid may have a temperature between 25° C. and 400° C. For instance, the fluid temperature may be between 50° C. and 100° C., between 100° C. and 150° C., or between 150° C. and 200° C. In other embodiments, the fluid temperature may be less than 25° C. or greater than 400° C.

As discussed herein, a downhole tool may include multiple actuation states. In such embodiments, when the downhole tool is in the desired location in the wellbore, one or more command signals may be transmitted to the downhole tool from the surface. The command signals may be transmitted through the fluid in the wellbore. For example, the command signals may be transmitted as variations in the flow rate of the fluid by, for instance, varying the flow rate from the pump at the surface. In other embodiments, the command signals may be transmitted in other ways, such as through a cable extending from the surface to the downhole tool, through variations in drill string rotation, through radio-frequency identification (RFID) tags, or in other manners.

When the command signals are transmitted by varying the flow rate of the fluid, a predetermined flow rate (e.g., between 1,000 L/min and 3,000 L/min) may first be established and measured by the downhole tool and stored in an electronics assembly of the downhole tool. Each command signal may include a single signal or "bit" or a plurality of bits. In some embodiments, each bit may include two possible values, (e.g., binary 0 or 1 values), or the bits may include more than two possible values (e.g., hexadecimal values, discrete values, etc.). When the bits are binary, a first potential value (e.g., a 0 value) for a bit may correspond to a flow rate (e.g., as measured by a sensor assembly) that is less than the predetermined flow rate (e.g., 2,000 L/min), and a second potential value (e.g., a 1 value) for the bit may correspond to a flow rate that is at or above the predetermined flow rate. Of course, the relationship of binary bits to the predetermined flow rate may also be reversed, and a 0 value may correspond to a flow rate above the predetermined flow rate, and a 1 value may correspond to a flow rate at or below the predetermined flow rate.

In some embodiments, the number of bits in each command signal may range from 1 to 100. For instance, there may be between 2 and 6, between 6 and 10, between 10 and 14, or between 14 and 25 bits in a command signal. For example, an illustrative command signal may include 13 bits. This many bits may be used to reduce the likelihood of an unintentional command signal being received, as the flow rate in the bore 116 may vary from time-to-time based on conditions that are independent of the pump at the surface. A portion of the bits (e.g., the first 7 bits) may represent the "preamble" of the command signal, and the remaining portion of the bits (e.g., the last 6 bits) may represent the "instructions" of the command signal. In at least one embodiment, two or more downhole tools may be run into the wellbore simultaneously or in sequence. The preamble, whether provided before or after an instructions portion of the command sequence, may act as an address to identify which particular downhole tool should receive and respond to the command signal, and the instructions may indicate an action to be taken by the particular tool. Thus, the preamble may indicate a particular component of a downhole tool, and the instructions may indicate an action to be taken by the particular component.

The duration of each bit (i.e., the length of time a flow rate is maintained) may be between 0.5 second and 10 minutes. For instance, the duration of each bit or other element of a command signal may be between 2 seconds and 8 seconds, between 5 seconds and 10 seconds, between 10 seconds and 20 seconds, between 20 seconds and 40 seconds, between 40 seconds and 60 seconds, between 1 minute and 2 minutes, between 2 minutes and 5 minutes, or between 5 minutes and 10 minutes. For example, with bits having a duration of 18 seconds each, a command signal including 13 bits may take about 234 seconds (or just under 4 minutes) to transmit and/or receive.

In a specific example, a command signal to actuate the cutter blocks 160 of the downhole tool 100 of FIGS. 1-3 into the active state may look like [1,0,1,0,1,1,1,0,1,0,1,0,1].

Thus, to transmit the command signal, an operator at the surface may turn the pump at the surface on (or up or down) to cause fluid to flow into the wellbore and through the bore 116 of the downhole tool 100. The flowing fluid may cause the impeller 220 to rotate. The sensor 250 in the sensor assembly 120 may measure the rate of rotation of the impeller 220, and this measurement may be transmitted from the sensor assembly 120 to the electronics assembly 140.

The electronics assembly 140 may determine the flow rate of the fluid using the rate of rotation of the impeller 220, as described herein. As the pump is turned on (or up or down) for the first 18 seconds, for example, the electronics assembly 140 may determine that the flow rate of the fluid is greater than the predetermined flow rate (e.g., 10 L/min), and may register a 1 for the first bit of the command signal. After another 18 seconds, the pump may be turned off (or down) at the surface for the next 18 seconds. As a result, the rate of rotation of the impeller 220 may decrease, and the electronics assembly 140 may determine that the flow rate of the fluid is less than the predetermined flow rate. The electronics assembly 140 may thus register a 0 for the second bit of the command signal. This may continue for each of the 13 bits.

After the final bit (e.g., 13th bit) of the command sequence and signal has been registered by the electronics assembly 140, the electronics assembly 140 may determine that the command signal satisfies a predetermined condition (e.g., a specific series of bits based on comparisons to the predetermined flow rate) and is therefore intended to actuate the cutter blocks 160 into the active state. The electronics assembly 140 may then communicate this command to the actuator assembly 150, which may cause the cutter blocks 160 to expand into the active state. For example, the actuator assembly 150 may cause a sleeve in the bore 116 to move, which may allow the hydraulic pressure of the fluid in the bore 116 to expand the cutter blocks 160. When the downhole tool 100 is to be deactivated, a series of changes in flow rate may be used to provide a deactivation sequence. In other embodiments, shutting off the fluid flow may automatically deactivate a hydraulically driven downhole tool 100. In some embodiments, the electronics assembly 140 may determine after a preamble portion of a command sequence (e.g., after the 7th bit) whether a command sequence is directed to a specific tool, or to which tool a sequence is directed. If the command sequence is not addressed to a component coupled to the electronics assembly 140, the actuator assembly 150 may not take any action.

As discussed herein, in addition to measuring the flow rate of the fluid in the bore 116, the sensor assembly 120 (and the electronics assembly 140) may measure additional properties of fluid in the wellbore such as the density and apparent viscosity of the fluid. The measured properties may be stored in the memory of the downhole electronics assembly 140 or transmitted to the surface in real-time via a MWD tool or the like (e.g., when the downhole tool 100 is connected to the MWD via a downhole communication bus). With knowledge of one or more of these fluid properties, flow conditions in the wellbore may be controlled when one or more of the properties (e.g., density or rheology) vary over depth, time, etc. Further, whether the sensor assembly 120 measures flow rate, additional properties, or both, the sensor assembly 120 may be resistant to erosion or degradation. Such degradation could occur in other sensors on account of the high flow rate and/or pressure of fluid and large particles (e.g., flake LCM or crushed carbonate) in the fluid.

In at least one embodiment, the measured fluid properties may be used to manage flow bypass through a motor in the downhole tool 100 or flow bypass to the annulus outside the downhole tool 100. For example, the flow conditions in the wellbore may be controlled to optimize the removal of cuttings made by the drill bit (not shown) and/or the cutter blocks 160 of the downhole tool 100. When the fluid is an aerated mud, the volumetric flow rate may vary as the depth in the wellbore varies. As such, the downhole volumetric flow rate may not be the same as the flow rate at the surface. With knowledge of one or more of the fluid properties downhole (e.g., flow rate, density, rheology), the flow rate at the surface may be maintained or varied to optimize the transport of cuttings to the surface. These properties may also be used to allow drilling through formations with a limited pressure margin.

In the description herein, various relational terms are provided to facilitate an understanding of various aspects of some embodiments of the present disclosure. Relational terms such as "bottom," "below," "top," "above," "back," "front," "left", "right", "rear", "forward", "up", "down", "horizontal", "vertical", "clockwise", "counterclockwise," "upper", "lower", and the like, may be used to describe various components, including their operation and/or illustrated position relative to one or more other components. Relational terms do not indicate a particular orientation for each embodiment within the scope of the description or claims. For example, a component of a bottomhole assembly that is described as "below" another component may be further from the surface while within a vertical wellbore, but may have a different orientation during assembly, when removed from the wellbore, or in a deviated borehole. Accordingly, relational descriptions are intended solely for convenience in facilitating reference to various components, but such relational aspects may be reversed, flipped, rotated, moved in space, placed in a diagonal orientation or position, placed horizontally or vertically, or similarly modified. Certain descriptions or designations of components as "first," "second," "third," and the like may also be used to differentiate between similar components. Such language is not intended to limit a component to a singular designation. As such, a component referenced in the specification as the "first" component may be the same or different than a component that is referenced in the claims as a "first" component.

Furthermore, while the description or claims may refer to "an additional" or "other" element, feature, aspect, component, or the like, it does not preclude there being a single element, or more than one, of the additional element. Where the claims or description refer to "a" or "an" element, such reference is not to be construed that there is just one of that element, but is instead to be inclusive of other components and understood as "at least one" of the element. It is to be understood that where the specification states that a component, feature, structure, function, or characteristic "may," "might," "can," or "could" be included, that particular component, feature, structure, or characteristic is provided in some embodiments, but is optional for other embodiments of the present disclosure. The terms "couple," "coupled," "connect," "connection," "connected," "in connection with," and "connecting" refer to "in direct connection with," or "in connection with via one or more intermediate elements or members." Components that are "integral" or "integrally" formed include components made from the same piece of material, or sets of materials, such as by being commonly molded or cast from the same material, or commonly machined from the same piece of material stock. Components that are "integral" should also be understood to be "coupled" together.

Although various example embodiments have been described in detail herein, those skilled in the art will readily appreciate in view of the present disclosure that many modifications are possible in the example embodiments without materially departing from the present disclosure. Accordingly, any such modifications are intended to be included in the scope of this disclosure. Likewise, while the disclosure herein contains many specifics, these specifics should not be construed as limiting the scope of the disclosure or of any of the appended claims, but merely as providing information pertinent to one or more specific embodiments that may fall within the scope of the disclosure and the appended claims. Any described features from the various embodiments disclosed may be employed in combination.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

While embodiments disclosed herein may be used in an oil, gas, or other hydrocarbon exploration nor production environment, such environment is merely illustrative. Systems, tools, assemblies, cutting inserts, methods, and other components of the present disclosure, or which would be appreciated in view of the disclosure herein, may be used in other applications and environments. In other embodiments, cutting inserts, cutting tools, milling tools, methods of milling, methods of cutting, methods of initiating a cutout, or other embodiments discussed herein, or which would be appreciated in view of the disclosure herein, may be used outside of a downhole environment, including in connection with other systems, including within automotive, aquatic, aerospace, hydroelectric, manufacturing, other industries, or even in other downhole environments. The terms "well," "wellbore," "borehole," and the like are therefore also not intended to limit embodiments of the present disclosure to a particular industry. A wellbore or borehole may, for instance, be used for oil and gas production and exploration, water production and exploration, mining, utility line placement, or myriad other applications.

Certain embodiments and features may have been described using a set of numerical values that may provide lower and/or upper limits. It should be appreciated that open-ended ranges including one value (e.g., at least 70% or up to 70%) are contemplated with such values, as is the combination of any two values defining a range having both lower and upper limits. A discrete value may also be used. Any numerical value in the description or claims is "about" or "approximately" the indicated value, and takes into account experimental error and variations that would be expected by a person having ordinary skill in the art. Any numbers, percentages, ratios, measurements, or other values stated herein are therefore intended to include the stated value as well as other values that are about or approximately the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least experimental error and variations that would be expected by a person having ordinary skill in the art, as well as the variation to be expected in a suitable manufacturing or production process. A value that is about or approximately the stated value and is therefore encompassed by the stated value may further include values that are within 5%, within 1%, within 0.1%, or within 0.01% of a stated value.

The abstract included with this disclosure is provided to allow the reader to quickly ascertain the general nature of some embodiments of the present disclosure. It is submitted with the understanding that it will not be used to interpret or limit the scope or meaning of the claims.

What is claimed is:

1. A method for measuring properties of a fluid in a wellbore, comprising:
    running a downhole tool into a wellbore, the downhole tool having a sensor assembly and an electronics assembly, the sensor assembly including:
        a housing made of a non-magnetic material, the housing defining an interior chamber;
        a shaft;
        at least one bearing around the shaft, the at least one bearing including a journal bearing having an inner sleeve and an outer sleeve, a radial clearance between an outer diameter of the inner sleeve and an inner diameter of the outer sleeve being between 1 μm and 1 mm;
        an impeller around the shaft and the at least one bearing, the impeller including a magnetized portion;
        a spring axially between the at least one bearing and the housing, the spring being configured to compress when a fluid applies an axial compressive force to the impeller; and
        a sensor configured to sense a rate of rotation of the impeller, measure the axial compressive force on the impeller, or both;
    pumping the fluid into the wellbore, the fluid causing the impeller to rotate, at least a portion of the fluid flowing through the radial clearance between the inner sleeve and the outer sleeve; and
    determining at least one property of the fluid using the electronics assembly and data related to the rotation of the impeller.

2. The method of claim 1, the at least one property of the fluid including a flow rate of the fluid, a viscosity of the fluid, or both.

3. The method of claim 2, wherein determining the at least one property of the fluid includes using a linear relationship between the flow rate of the fluid and the rate of rotation of the impeller.

4. The method of claim 1, the sensor assembly further including:
    a hydraulic brake coupled to the impeller, the hydraulic brake including at least one fin that extends axially and substantially parallel to a central longitudinal axis of the impeller, the at least one fin being configured to slow the rate of rotation of the impeller when the hydraulic brake is coupled to the impeller.

5. The method of claim 4, the impeller being a first impeller, and the sensor assembly further including:
    a second impeller not coupled to the hydraulic brake coupled to the impeller, or to any other hydraulic brake in the sensor assembly; and
    a second sensor configured to sense a rate of rotation of the second impeller.

6. The method of claim 5, wherein determining at least one property of the fluid includes determining a flow rate and a density of the fluid includes using data related to the rate of rotation of the first and second impellers.

7. The method of claim 4, further comprising:
    measuring the rate of rotation of the impeller during a first time period in which the hydraulic brake is coupled to the impeller;
    decoupling the hydraulic brake from the impeller; and
    measuring the rate of rotation of the impeller during a second time period in which the hydraulic brake is decoupled from the impeller.

8. The method of claim 1, further comprising:
    varying a flow rate of the fluid;
    detecting one or more changes in the flow rate of the fluid using the sensor assembly;
    comparing the flow rate of the fluid as the one or more changes are detected to a predetermined flow rate; and
    actuating a mechanical device from a first state to a second state when the one or more changes in the flow rate satisfy a predetermined condition relative to the predetermined flow rate.

9. The method of claim 8, wherein varying the flow rate of the fluid includes forming a command signal having a plurality of bits, each bit corresponding to either a first value where the flow rate of the fluid is greater than the predetermined flow rate, or a second value where the flow rate of the fluid is below the predetermined flow rate.

10. The method of claim 9, wherein actuating the mechanical device includes:
    interpreting a first set of the plurality of bits as a preamble that identifies a component of the downhole tool; and
    interpreting a second set of the plurality of bits as instructions for actuation of the mechanical device.

* * * * *